June 27, 1961 E. B. PARKER Plant Pat. 2,064
CHRYSANTHEMUM PLANT
Filed Feb. 8, 1960
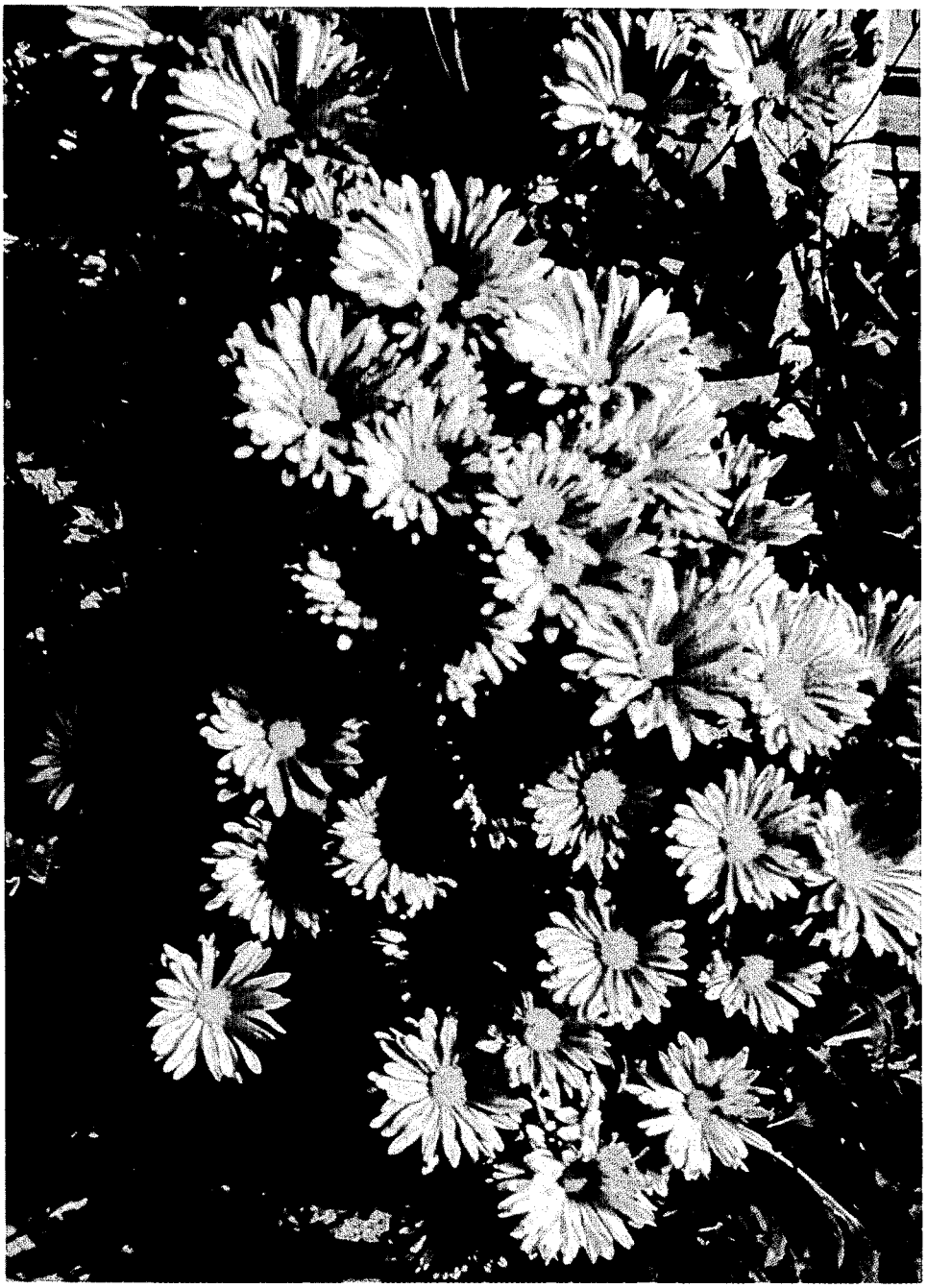
INVENTOR.
ELIZABETH B. PARKER
By John Joseph Hall
ATTORNEY.

United States Patent Office

Plant Pat. 2,064
Patented June 27, 1961

2,064
CHRYSANTHEMUM PLANT

Elizabeth B. Parker, 2937 Glendower Ave.,
Los Angeles, Calif.

Filed Feb. 8, 1960, Ser. No. 7,500
1 Claim. (Cl. 47—60)

The present invention relates to a new and distinct variety of chrysanthemum plant obtained by crossing the unpatented variety "Lilac Spoon" with an unnamed and unpatented bronze daisy chrysanthemum. The object of this crossing was to obtain a new and different variety of chrysanthemum having a new and unusual color and a fragrance which would persist for a relatively long period of time.

The variety resulting from the above crossing is an entirely new and distinct chrysanthemum plant with characteristics which distinguish it from either of its parents and from any other variety of chrysanthemum plant known to me.

One of the distinguishing characteristics of my new variety is the prominent old rose fragrance which lasts for the life of the flower, four to six weeks, even when the flowers are cut. Another outstanding characteristic is the unusual color of the petals, Phlox Purple throughout the entire length of the inside of the petals of the mature flower, and Phlox Pink throughout the entire length of the outside of the petals of the mature flower.

During the budding stage, the present variety has a bud with a Pompeian Red color. As the petals begin to open, the center of the elongated bud shows. The center has a color of Ochraceous Buff.

The blooming period of my new variety begins in the last week of October and extends until the middle of December under the climatic conditions prevailing in Los Angeles, California. Cultivation of this new variety was accomplished entirely in the frost free climate of Los Angeles, California. My new variety has proved to be mildew resistant upon exposure to mildew. The locale of such exposure was Los Angeles, California, and the exposure involved continuous and close proximity of my new variety to mildewed plants of other varieties under moist conditions and temperatures varying from 38 to 85 degrees Fahrenheit, over a period of several months.

I have performed asexual reproduction of my new variety of chrysanthemum plant by cuttings through several succeeding generations at Los Angeles, California. All of the foregoing characteristics and distinguishing features of my new variety were transmitted true to form through each of the succeeding generations.

The accompanying color photograph shows typical specimens of the vegetation, flowers, and buds of my new variety.

A detailed description of my new variety follows, with all references to color being in accordance with Ridgway's Color Standards and Nomenclature.

Parentage: The unpatented variety "Lilac Spoon" crossed with an unnamed and unpatented bronze daisy.
Classification: Single daisy type.
Growth: A natural cascade with stems 34 to 36 inches on cascade. Must be kept low if an upright is desired.
Cold resistance: No testing was made of cold resistance since the plant was cultivated in a frost free climate.
Blooming period: From the last week in October until the middle of December under the climatic conditions prevailing in Los Angeles, California.
Mildew resistance: The plant is not sensitive to mildew.

*Flower*

Bud:
*Color.*—Pompeian Red, Plate 13.
Bud center: Does not show until petals begin to open.
*Color.*—Ochraceous Buff, Plate 15.
Bloom:
*Size.*—2½ to 3 inches in diameter.
*Stem.*—Willowy with natural cascade. Becomes upright with support.
*Form.*—Single daisy.
*Petalage.*—2 to 3 rows of petals.
*Fragrance.*—An old rose fragrance which lasts for the life of the flower, 4 to 6 weeks even when cut.
*Petals.*—Texture—long, smooth, velvety. Form—petals are square at the distal tip.
*Color.*—Center—Ochraceous Buff, Plate 15. Inside of petals, for the entire length: Phlox Purple, Plate 11. Outside of petals, for the entire length: Phlox Pink, Plate 11.

*Plant*

Form: Usually a single stem which makes an individual spray.
Growth: Vigorous and tall.
Foliage: Lush and mildew resistant.
*Size.*—An elongated narrow leaf 2½ to 3½ inches long.
*Quantity.*—Generous.
*Color.*—*Upper side*—Dark Cress Green, Plate 3. *Reverse side*—Pois Green, Plate 21.
*Texture.*—Fine grained.

I claim:

A new and distinct variety of chrysanthemum plant, substantially as shown and described herein, characterized particularly as to novelty by the old rose fragrance of its flowers, the relatively long duration of the fragrance, the distinctive Phlox Purple coloration of the entire inside of the petals of the open flower, the distinctive Phlox Pink coloration of the entire outside of the petals of the open flower, and the resistance to mildew of the plant.

No references cited.